US005750184A

United States Patent [19]
Imburgia

[11] Patent Number: 5,750,184
[45] Date of Patent: May 12, 1998

[54] UNITARY BIOLOGICAL INDICATOR FOR GASEOUS STERILANTS AND PROCESS

[75] Inventor: Richard Imburgia, Vernon Hills, Ill.

[73] Assignee: Pharmaceutical Systems, Inc., Mundelein, Ill.

[21] Appl. No.: 574,642

[22] Filed: Dec. 19, 1995

[51] Int. Cl.[6] ...................................... G01N 21/00
[52] U.S. Cl. .......................... 427/2.13; 435/31; 435/38; 435/810; 435/287.4; 435/287.6; 422/55; 422/56; 422/58; 422/86
[58] Field of Search ............................. 435/287.4, 288.1, 435/287.6, 18, 19, 21, 23, 24, 31, 38, 810; 422/55, 56, 58, 60, 86; 427/2.13

[56] References Cited

U.S. PATENT DOCUMENTS

| | | | |
|---|---|---|---|
| 2,998,306 | 4/1961 | Huyck et al. | 435/287.4 |
| 3,440,144 | 4/1969 | Andersen . | |
| 3,661,717 | 5/1972 | Nelson | 435/287.4 |
| 3,711,378 | 1/1973 | Kereluk | 435/287.4 |
| 3,752,743 | 8/1973 | Henshilwood | 435/287.4 |
| 4,291,122 | 9/1981 | Orelski | 435/31 |
| 4,304,869 | 12/1981 | Dyke | 435/296 |
| 4,416,984 | 11/1983 | Wheeler, Jr. | 435/31 |
| 4,461,837 | 7/1984 | Karle et al. | 435/296 |
| 4,528,268 | 7/1985 | Anderson et al. | 435/31 |
| 4,579,823 | 4/1986 | Ryder | 435/296 |
| 4,580,682 | 4/1986 | Gorski et al. | 206/569 |
| 4,596,773 | 6/1986 | Wheeler, Jr. | 435/31 |
| 4,717,661 | 1/1988 | McCormick et al. | 435/31 |
| 4,732,850 | 3/1988 | Brown et al. | 435/31 |
| 4,740,475 | 4/1988 | Paul | 434/165 |
| 4,741,437 | 5/1988 | Gorski et al. | 206/222 |
| 4,743,537 | 5/1988 | McCormick et al. | 435/296 |
| 4,828,797 | 5/1989 | Zwarun et al. | 422/55 |
| 4,839,291 | 6/1989 | Welsh et al. | 435/296 |
| 4,883,641 | 11/1989 | Wicks et al. | 422/50 |
| 4,885,253 | 12/1989 | Kralovic | 435/296 |
| 4,914,034 | 4/1990 | Welsh et al. | 435/296 |
| 4,935,371 | 6/1990 | Rickloff | 435/296 |
| 4,937,115 | 6/1990 | Leatherman | 428/36.4 |
| 4,965,047 | 10/1990 | Hammond | 435/31 |
| 5,011,663 | 4/1991 | Innocenti | 422/102 |
| 5,066,464 | 11/1991 | Augurt | 422/58 |
| 5,073,488 | 12/1991 | Matner et al. | 435/31 |
| 5,084,239 | 1/1992 | Moulton et al. | 422/22 |
| 5,115,166 | 5/1992 | Campbell et al. | 315/111.21 |
| 5,167,923 | 12/1992 | Van Iperen | 422/58 |
| 5,223,401 | 6/1993 | Foltz et al. | 435/18 |
| 5,270,650 | 12/1993 | Schenz et al. | 324/308 |

FOREIGN PATENT DOCUMENTS 1182729   9/1982   Canada ............................... 150/16.2

OTHER PUBLICATIONS

"Biological Indicator for Dry–Heat Sterilization, Paper Strip," *U.S. Pharmacopeia XXII, Official Monograph*, pp. 170–171.

Davenport, "Design and Use of a Novel Peracetic Acid Sterilizer for Absolute Barrier Sterility Testing Chambers," *Journal of Parenteral Science & Technology*, 43(4), pp. 158–166 (1989).

(List continued on next page.)

*Primary Examiner*—David A. Redding
*Attorney, Agent, or Firm*—Majestic, Parsons, Siebert & Hsue, P.C.

[57] ABSTRACT

A biological indicator is formed from two members (or a sheet with one portion folded onto another portion) which are sealed together and form a pathway having three sections. One section opens to the exterior and is preferably configured as a tortuous path. A middle pathway portion downstream of the tortuous path houses a frangible ampule. The frangible ampule contains growth medium for microorganisms. An interior pathway portion (most downstream from the exterior) houses a carrier inoculated with spores of a microorganism. The biological indicator preferably is prepared by a process in which a thermoplastic sheet has the pathway formed by thermoforming and the sealing is by heat sealing.

14 Claims, 3 Drawing Sheets

OTHER PUBLICATIONS

Macek, "Biological Indicators –A U.S.P. Review," *Bulletin of the Parenteral Drug Association,* 26(1), pp. 18–25 (1972).

"Biological Indicators," U.S. Pharmacopeia XXII, Official Monograph, pp. 1625–1626.

Code of Federal Regulations, Title 21: Food and Drug Administration, Department of Health and Human Services, Subchapter H –Medical Devices, Part 880.2800, pp. 322–323.

"Biological Indicator for Steam Sterilization, Paper Strip," *U.S. Pharmacopeia XXII, Official Monograph,* pp. 173–175.

"Biological Indicator for Ethylene Oxide Sterilization, Papear Strip," *U.S. Pharmacopeia XXII, Official Monograph,* pp. 171–173.

Premark Notification to Food and Drug Administration, Jul. 24, 1992.

Miyauchi et al., "Microbiological Studies on Heat Processed Foods: 1. Survival of Microorganisms in Commercial Canned Foods," *Biological Abstract,* 72(5), Abstract No. 30742 (1981).

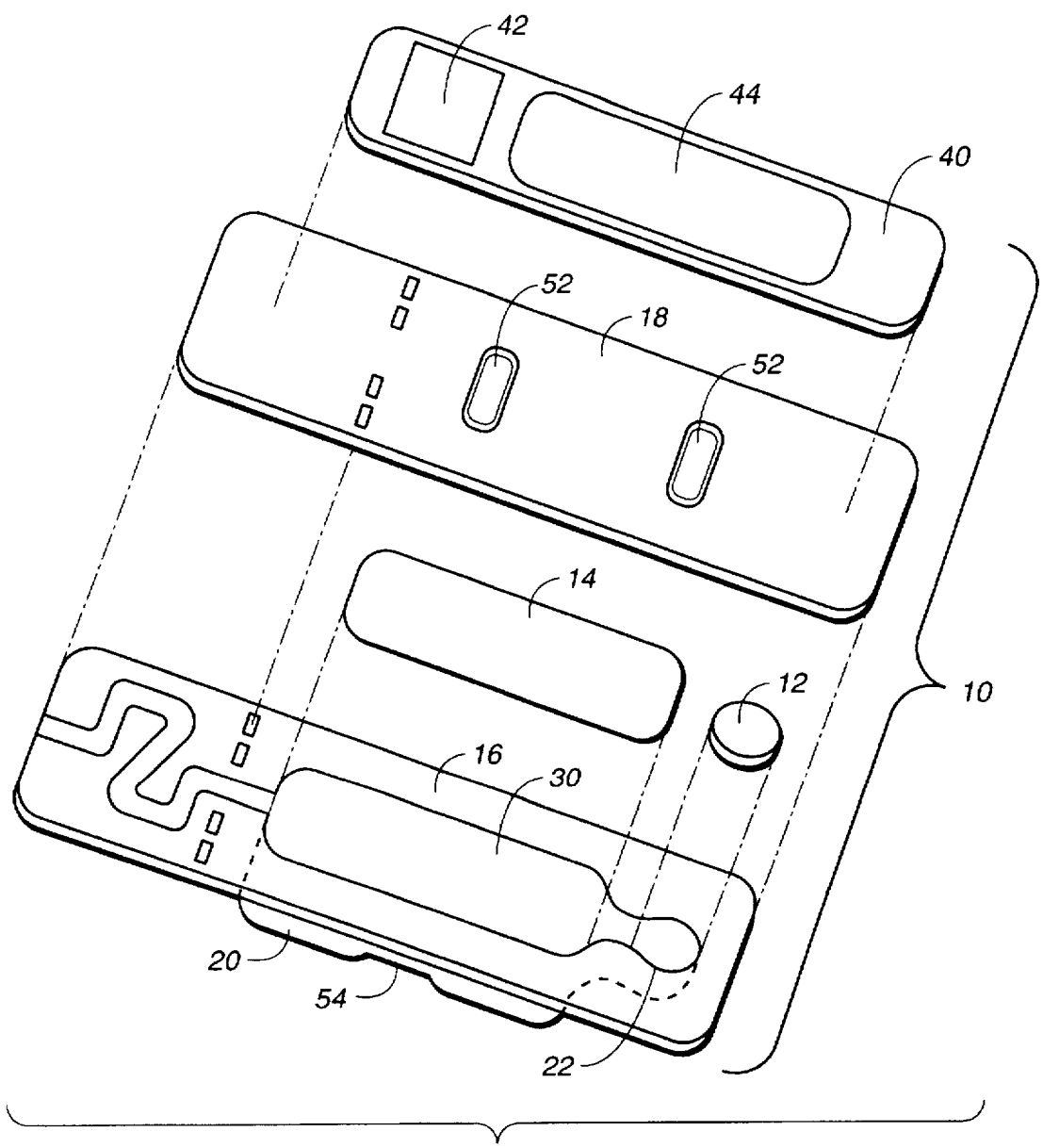
FIG._1

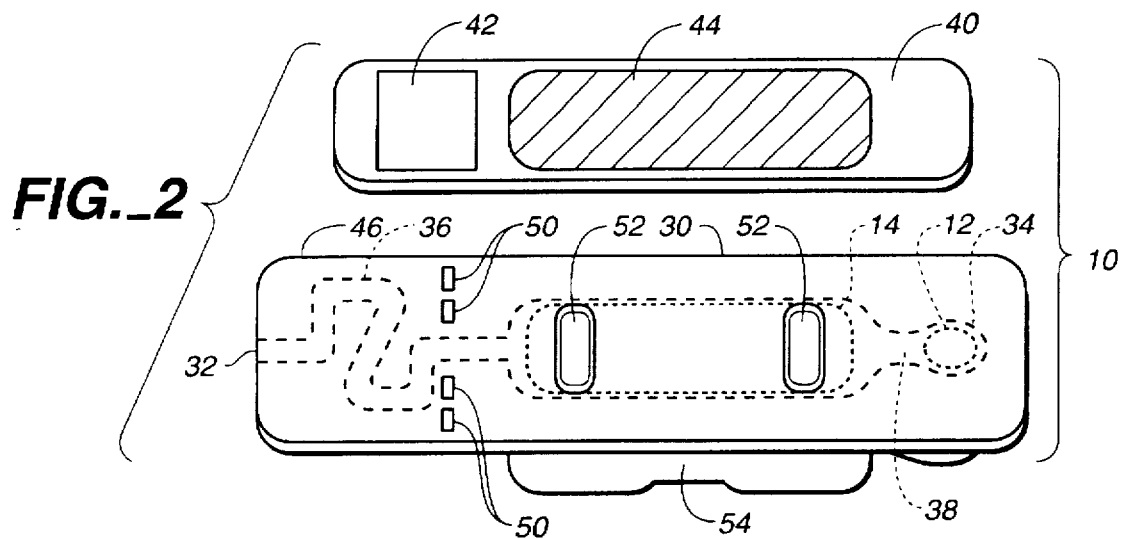
FIG._2
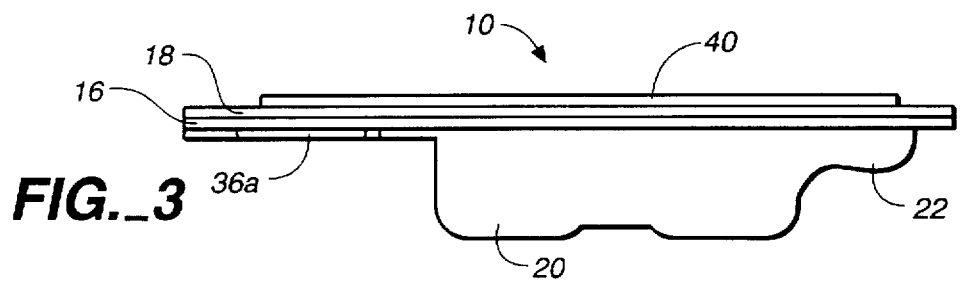
FIG._3
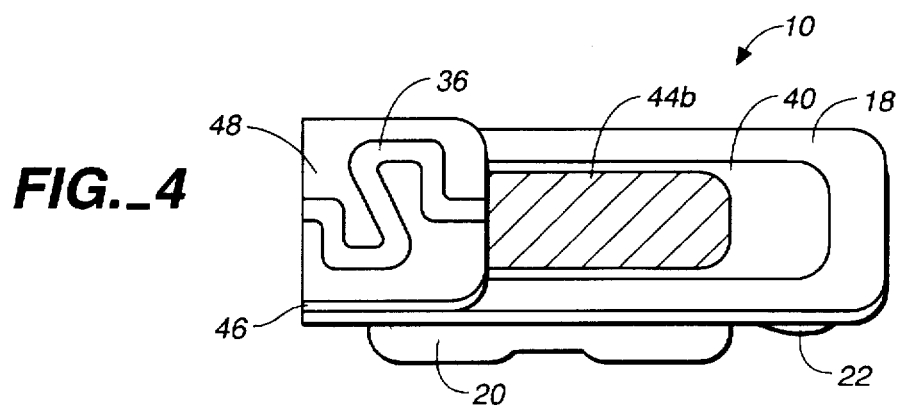
FIG._4

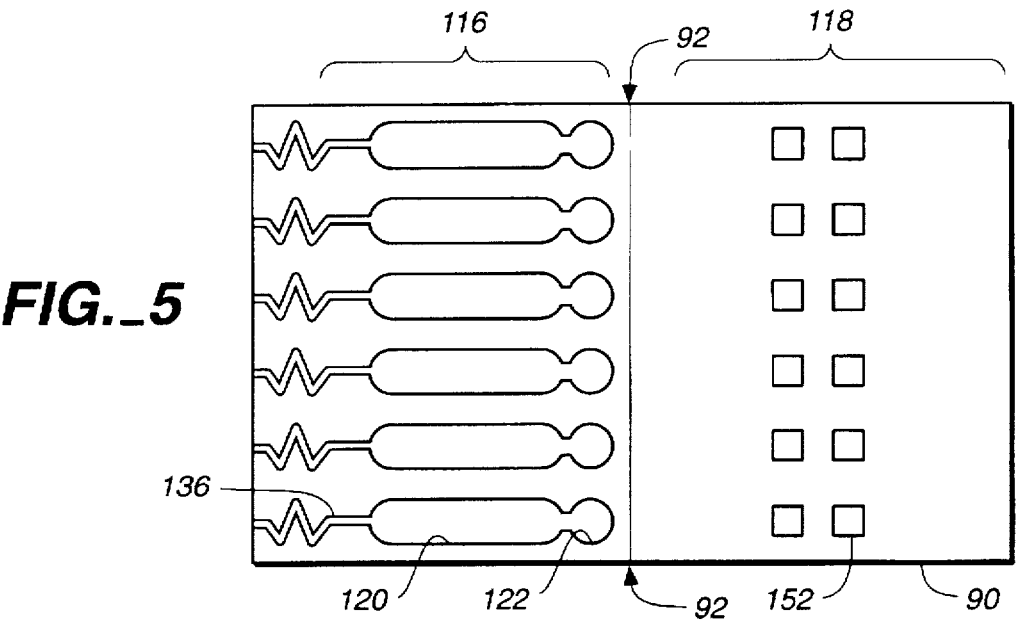
FIG._5
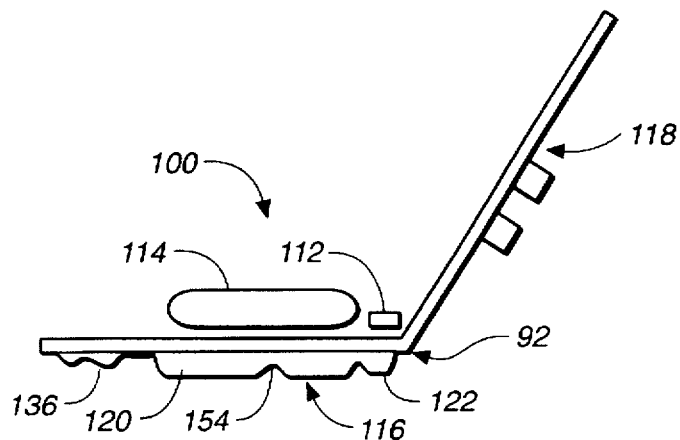
FIG._6
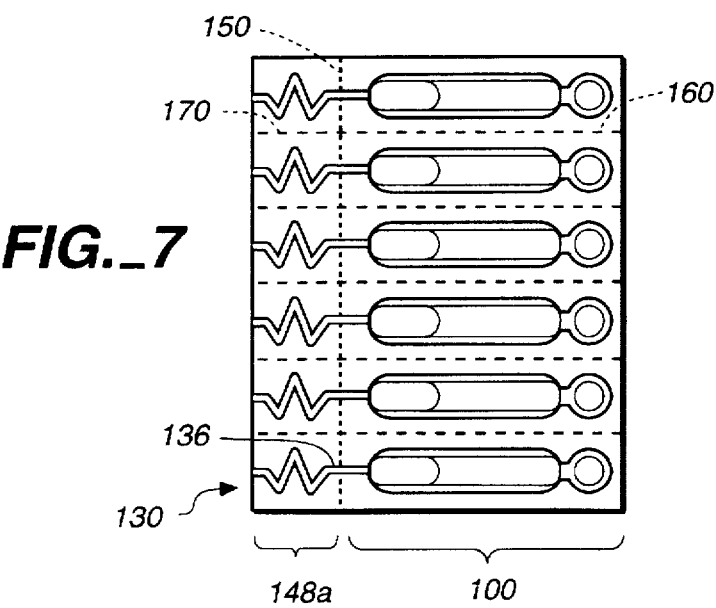
FIG._7

UNITARY BIOLOGICAL INDICATOR FOR GASEOUS STERILANTS AND PROCESS

FIELD OF THE INVENTION

The present invention generally involves biological indicators for sterilizing processes, and more particularly the use of biological indicators where the components necessary for monitoring a sterilization cycle are all contained in one conveniently manipulated and easily manufactured unit. The present invention also involves the process for preparing such biological indicators.

BACKGROUND OF THE INVENTION

It is important that the instruments and supplies used in medical procedures are free of contaminating microorganisms. Thus, processes have been developed for sterilization such as those using dry heat, steam, and ethylene oxide.

Two recently issued patents, of common assignment herewith, illustrate an emerging use of oxidizing gases for sterilization, which is replacing the use of ethylene oxide. Thus, U.S. Pat. No. 5,084,239, issued Jan. 28, 1992, inventors Moulton et al., describes a process in which an antimicrobial agent treatment is alternated with a downstream plasma treatment. The antimicrobial agent may be peracetic acid vapor delivered at subatmospheric pressure conditions. U.S. Pat. No. 5,115,166, issued May 19, 1992, inventors Campbell et al., describes a plasma sterilizing apparatus and method where an article to be sterilized is exposed to active species derived from a gas plasma.

Biological indicators are used with sterilizing processes. The *U.S. Pharmacopeia XXII, Official Monograph*, pp. 1625–1626 defines a biological indicator ("B.I.") as "a characterized preparation of specific microorganisms resistant to a particular sterilization process. It is used to assist in the qualification of the physical operation of sterilization apparatus in the development and establishment of a validated sterilization process for a particular article, and the sterilization of equipment, materials, and packaging components for aseptic processing. It may also be used to monitor a sterilization cycle, once established, and periodically in the program to revalidate previously established and documented sterilization cycles. B.I.'s typically incorporate a viable culture of a known species of microorganism."

A biological indicator generally incorporates three essential components: a specific number of viable microorganisms; a carrier onto which the organisms are inoculated; and a package surrounding the organisms and carrier to prevent contamination of the carrier with foreign microorganisms. In addition, many biological indicators incorporate a means for testing the viability of the organisms after exposure to a sterilizing process without opening the package. These are known as unitary biological indicators or self-contained biological indicators.

A variety of biological indicators have been suggested for use with different sterilization processes. For example, U.S. Pat. No. 4,304,869, issued Dec. 8, 1981, inventor Dyke, describes a capped tube including a glass ampule that contains nutrient medium. Also within the vial (but exterior the glass ampule) is a carrier disk inoculated with spores. When the cap is manipulated, the glass ampule is ruptured by a wedging action, and the spores are exposed to the nutrient medium. The vial contents can then be incubated. The nutrient medium preferably includes a pH indicator so that a color change resulting from bacterial growth indicates a positive test result (growth).

U.S. Pat. No. 4,461,837, issued Jul. 24, 1984, inventors Karle et al., describes a container for test spores and a frangible ampule containing growth medium. A closure initiates rupture of the ampule when it is moved into a sealing engagement with the container.

U.S. Pat. No. 4,743,537, issued May 10, 1988, inventors McCormick et al., describes a self-contained biological indicator with a flexible cylindrical tube having a submicron screen at one end, and containing a wick carrying spores and also an ampule containing growth medium and a pH indicator material. The ampule can be broken by applying pressure through the flexible side of the device.

New biological indicators continue to be sought with less expensive and readily accomplished production and/or with more convenient manipulation, all the while providing reliable and consistent results in qualifying or monitoring particular sterilizing processes.

SUMMARY OF THE INVENTION

In one aspect of the present invention, a self-contained, or unitary, biological indicator includes a carrier with a species of microorganism that has been selected for resistance to a particular sterilization process (or processes). The carrier is inoculated with the appropriate microorganism, preferably in the form of bacterial spores, and is disposed along a pathway formed by opposed first and second members. The pathway extends between an open end and a closed end, and is configured as a tortuous path adjacent to the open end. The microorganisms are downstream of the tortuous path a spaced distance from the open end. A frangible ampule, which includes growth medium for the microorganisms, is also disposed along the pathway beneath a deformable portion of the first member. When sufficient externally applied pressure is placed against the deformable portion, the ampule ruptures and the microorganism spores are placed in contact (by fluid communication) with the growth medium.

The opposed first and second members can be separate or be from a single thermoformable sheet. A depression is formed in the first member, sometimes called a cavity member. This first member is joined to a second member, sometimes called a backing member. When the two members are joined together, the pathway is defined.

The pathway preferably includes three sections, each with its own shape and function. The section located furthest into the device, or away from the surrounding environment, can house the inoculated carrier. The section located closest to the surrounding environment, at the inlet to the device, is configured as a tortuous path. Between these two sections can be the ampule compartment to house a frangible ampule that contains growth medium for the microorganisms.

The first member is composed of a flexible material, such that when sufficient externally supplied pressure is applied to the ampule section of the device, the ampule ruptures and immerses the microorganisms on the carrier in the growth medium. The inoculated carrier and frangible ampule are placed in the formed cavity member prior to placement of the backing member and its affixation to the cavity member. After joining the two members, the carrier and ampule are housed within the device. The first and second members may be folded near the open end of the pathway to form a flap which crimps the pathway between the microorganisms and the open end. The folded position is used when the microorganisms are contacted with growth medium after rupture of the ampule. Thus the fold provides additional protection against contamination from foreign microorganisms and evaporation of liquid when incubating the biological indicator.

An additional preferred component for inclusion with the inventive biological indicators is a chemical indicator that may be affixed to the exterior of the indicator to visually indicate whether exposure to a sterilization cycle has occurred, or may be disposed in the pathway.

In another aspect of the present invention an apparatus, useful in monitoring a sterilizing apparatus or sterilizing process, comprises a plurality of indicator units formed with a common wall and being attached to each other. Each unit is separable from an adjacent unit along a common edge. Each unit includes a carrier inoculated with a selected number of viable organism spores and a pathway in which the carrier is disposed. Each pathway is defined by the common wall and a second wall. Each pathway is a spaced distance from the common edge and maintains structural integrity when units are separated. In this embodiment of the invention, any one indicator unit may include a different number of viable organism spores (or a different type of viable organism spores), than another of the units. This embodiment is preferably manufactured with a plurality of the first and second members thermoformed from a single sheet of plastic. Thus, the apparatus with a plurality of indicator units as already described may be manufactured from a single sheet of thermoformable material, which permits efficient, large quantity manufacture.

In yet another aspect of the present invention, a process of making a biological indicator comprises providing a cavity member sheet of deformable material, deforming the sheet to begin forming a pathway having three portions, disposing a frangible ampule in one pathway portion and a carrier in another pathway portion, and sealing a backing sheet to the cavity member sheet to complete formation of the pathway.

Biological indicator embodiments of the invention are conveniently manipulated and easily manufactured, with other objects and advantages likewise becoming apparent from reading the detailed description.

BRIEF DESCRIPTION OF THE DRAWINGS

FIG. 1 is an exploded, perspective view of an inventive embodiment;

FIG. 2 is a partially assembled embodiment;

FIG. 3 is the side view of a fully assembled embodiment;

FIG. 4 is a perspective view of an embodiment prepared for incubation;

FIG. 5 is a plan view of another inventive embodiment in the process of manufacture;

FIG. 6 is a side view of the FIG. 5 embodiment, but at a more advanced stage of production; and FIG. 7 is a fully assembled and completed manufacture of the other inventive embodiment.

DETAILED DESCRIPTION OF THE PREFERRED EMBODIMENTS

At the heart of all biological indicators (sometimes abbreviated "B.I.") are the microorganisms chosen to be resistant to a particular sterilization process or processes. Thus, the unitary, or self-contained, biological indicators of this invention incorporate a viable culture of a known species of microorganism, preferably in the form of microbial spores. Suitable microorganisms are readily available from, for example, a depository such as the American Type Culture Collection, 12301 Parklawn Drive, Rockville, Md. 20852. Preferred are thermotolerant organisms, such as Bacillus species.

Bacterial spores, rather than the vegetative form of the organisms, are used because vegetative bacteria are known to be relatively easily killed by sterilizing processes. Spores also have superior storage characteristics as they can remain in their dormant state for years. Thus, sterilization of a large inoculum of a standardized spore strain provides a high degree of confidence that inactivation of all microorganisms in the sterilizing chamber has occurred.

The microorganism selected should be highly resistant to the particular sterilization process contemplated. Accordingly, different embodiments of the invention may utilize different microorganisms, depending upon the sterilization process or processes for which the particular embodiment is intended. A particular strain of microbial spores selected for use as a biological indicator and resistant to one sterilization process may not necessary be suitable for other sterilization processes. Thus, each form of biological indicator must be validated for the particular application contemplated.

For example, if the biological indicator is intended to be used for monitoring the efficacy of steam sterilization, the microorganism can be Bacillus stearothermophilus since this organism is known to be highly resistant to the steam used in such a sterilization process. If the sterilization process contemplated is ethylene oxide, then the microorganism chosen can be from a strain of Bacillus subtilis, such as subspecies niger. Where the biological indicators are intended to qualify or monitor plasma generated species or oxidizing gases (such as, for example, peracetic acid), then embodiments of the invention preferably use spores of Bacillus circulans. U.S. Pat. No. 5,115,166 particularly describes a plasma generated gas mixture while U.S. Pat. No. 5,084,239 describes a two-step process, one step of which can use peracetic acid vapor as sterilant. Both patents are hereby incorporated herein by reference. Although the inventive biological indicators were developed for preferred use with a synergistic, two-step oxidizing gas sterilization process such as described in the just noted patents, they are broadly useful with and may readily be adapted for other gaseous sterilants and other gaseous sterilizing processes by selecting a microorganism suited for the particular process.

As will be more fully described hereinafter, in one embodiment of the invention where there are a plurality of indicator units formed with a common wall, the units can differ from one another such as by having different populations of spores or by having different spore organisms. Spore populations will typically be in the range of about $10^2$ to about $10^8$. With different populations of spores from one unit to the next in the plurality of indicator units, the user can study factors such as the log reduction value obtained during a sterilization cycle. However, in most usual applications there will be a consistent population of the same microorganism.

The carrier on which spores are inoculated is simply a means by which a selected number of indicator organisms are held and positioned within the B.I. Carriers can vary widely in the choice of materials and shapes so long as this function is served. Typically, carriers are formed of materials such as filter paper, which has excellent storage stability. Carriers made of metals such as aluminum or stainless steel may also be used.

Before inoculating spores onto the carrier, a heat shock step is desirably performed. Heat shock is a sublethal thermal treatment given to aqueous spore suspensions to modify enzymes in preparation for germination. Thus, a preferred sequence is a heat shock step, cooling, diluting the liquid spore suspension, and then inoculating carriers.

The carrier can be quite simply inoculated with spores by preparing an aqueous suspension with the desired spore concentration and pipetting an aliquot onto the carrier. Such operations are described in the *U.S. Pharmacopeia XXIII* monographs on "Biological Indicator for Steam Sterilization, Paper Strip" and "Biological Indicator for Ethylene Oxide Sterilization, Paper Strip." After inoculation, the carriers are dried.

Turning to FIG. 1, a biological indicator 10 embodiment in accordance with the invention is illustrated in exploded perspective. A carrier 12 on which spores are inoculated and an ampule 14, that is frangible such as by being formed of thin glass, are both held in respective cavities formed by opposed first member 16 and second member 18.

First member 16 preferably is formed of a flexible plastic and has at least one deformable portion shaped as cavity 20 that will lie adjacent to the frangible ampule 14 when first and second members 16, 18 are joined together, as will be hereinafter more fully described and illustrated.

FIG. 3 best illustrates the cavity 20 and another cavity 22 in which carrier 12 can be disposed. Suitable flexible plastic (polymeric) materials from which first member 16 may be formed include, for example, polypropylene and polypropylene copolymers, nylons, thermoplastic polyethylene terphthalate, and fluoroplastics.

When the inventive biological indicator is to be used in monitoring a sterilization process that does not involve high temperatures, then substantially any of the suitable flexible plastic materials may be used. For example, the earlier discussed plasma process does not require elevated temperatures. However, if the biological indicator is contemplated for use in a sterilization process requiring elevated temperatures, then the plastic will be selected from those materials having higher melting points, such as polycarbonate. The second member 18 may be selected from a wide variety of materials, but for manufacturing convenience and cost considerations as will be hereinafter more fully described, the second member 18 is preferably also formed of the same material or a similar as that used for first member 16.

One method for molding the first member to create cavities 20, 22 is through the use of a thermoforming process where materials are heated and then drawn or pushed into an appropriately shaped die using a vacuum or over-pressure. On contacting the die, the material cools and retains its new shape. This is just one method that could be used. Other standard methods of plastic forming or molding may also be used.

Deformable portion forming cavity 20 of first member 16 is preferably formed in a shape that generally corresponds with ampule 14 so as to receive the ampule 14 fairly snugly therein, and as already noted similarly first member 16 preferably has cavity 22 shaped so as to receive carrier 12 therein. First member 16 is configured to conform to the shapes of ampule 14 and carrier 12 such that sufficient clearance exists to allow a path for gas to come into contact with the spores on the carrier. Thus, although typically rather snugly sandwiched between first and second members 16, 18, the ampule should not prevent gases from passing or block the passage from the exterior to the carrier 12.

Still with reference to FIG. 1, one can readily understand that manufacturing and assembling embodiment 10 can be performed efficiently, since ampule 14 and carrier 12 may be readily dropped into cavities 20 and 22 formed in first member 16 as has been described. Second member 18 is then placed into contact with (for example, is lowered onto) first member 16 and adhered thereto, by conventional techniques, such as heat sealing or adhesive bonding. Examples of heat sealing include sealing through use of heated rollers, sealing through use of heated bars, radio frequency sealing, and ultrasonic sealing.

So adhered and bonded together, the first and second members will form a pathway, as will now be described with reference to FIG. 2.

Turning to FIG. 2, a pathway 30 is defined between an open end 32 and a closed end 34. Fluid, typically gas or vapor, can flow from the surrounding environment (here contemplated as being the sterilizing process fluid environment) into pathway 30 at open end 32, and then will proceed through a portion of pathway 30 adjacent to open end 32 that is configured as a tortuous path 36. The tortuous path 36 preferably includes at least one, more preferably a plurality of right angles or angles greater than 90°. Turning to FIG. 3, in the simpler and preferred version of the biological indicator embodiment as illustrated, the tortuous path 36 is actually formed by the first and second members 16, 18 such as where the first member 16 has a channel 36a formed in a serpentine shape.

The tortuous path 36 can also be contained and held by first and second members 16, 18, such as where a diffuser (not illustrated) is inserted in pathway 30 adjacent to open end 32. For example, suitable diffuser materials would have holes, pores, or interstices permitting diffusion along tortuous paths. Commercially available microporous filters could be used. Another suitable material is formed by a β-irradiated, chemically etched membrane, such as is commercially available as Nucleopore or Poretics filters, which membranes also define tortuous paths. Paper or cotton diffusers could also be used.

Returning to FIG. 2, the carrier 12 with its spores is disposed along pathway 30 a spaced distance from open end 32 and downstream of tortuous path 36. The frangible ampule 14 is likewise downstream of the tortuous path 36. As shown, ampule 14 is upstream with respect to carrier 12. These positions could be reversed, although this is not preferred. In either event, the ampule 14 and carrier 12 are disposed along the pathway 30 to permit the growth medium in ampule 14 to come into contact with carrier 12 when ampule 14 is ruptured, such as via passageway 38.

Ampule 14 contains an aqueous growth promoting medium such as tryptic soy broth. When ampule 14 is ruptured and the fluid contacts carrier 12, the spores will be moistened and exposed to nutrients. The B.I. is then held at a temperature suitable for the growth of the indicator organism. The viability of spores is indicated under growth promoting conditions by microorganism growth.

Typically, when spores are bathed with an aqueous solution containing appropriate nutrients and incubated for seven days, then any viable spores will grow and exhibit metabolic activity. Such activity can be indicated through use of a suitable growth detector, such as a pH indicator.

Formulations for culture media are widely known, as are various pH or oxidizing-reduction dyes as growth detectors. Many are listed in *U.S. Pharmacopeia XXIII*. An illustrative formulation for the growth media with preferred and more preferred ranges are listed below, which has been used with several different microorganisms, including *B. circulans*.

|  | More Preferred (g/l) | Preferred Range (g/l) |
|---|---|---|
| Pancreatic Digest of Casein (Peptone) | 5.7 | 5.0–7.0 |
| Papaic Digest of Soy Meal (Peptone) | 1.0 | 0.5–1.5 |
| Dextrose | 3.8 | 3.5–4.5 |
| Soluble Starch | 1.0 | 0.5–1.5 |
| Dipotassium Phosphate | 0.8 | 0.8–1.0 |
| Bromcresol Purple | 0.01 | 0.008–0.018 |
| Distilled Water | Balance | Balance |
| Pre-Sterilization pH (adjust with NaOH) | 7.7 | 7.5–7.9 |
| Post-Sterilization pH | 7.4 | 7.2–7.6 |

Sterilize at 250° F. (121.1° C.) for 15 minutes.
Storage temperature prior to sterilization: 2–8° C.
Maximum time between formulation and sterilization of the medium: 8 hours.

When one uses a color change to indicate spore growth and thus viability, it is preferable that at least a portion of first member 16 or second member 18 adjacent to carrier 12 be clear or of a color such that the color change of the growth medium can be readily observed.

With reference to FIG. 2, a label 40 is preferably included as a component of B.I. 10. Label 40 preferably includes an adhesive strip 42 and a chemical indicator 44 (shown as 44a due to the color condition, as will be more fully explained). The adhesive strip 42 is useful to secure the flap portion which substantially closes the passageway 36 upstream of carrier 12 from any further communications from the exterior through tortuous path 36, as will also be more fully described hereinafter. Chemical indicator 44 is useful to indicate when the biological indicator 10 has been exposed to sterilizing conditions.

Since the response of chemical indicator 44 may occur in the absence of one or more essential sterilization components, the response is not necessarily an indication of sterility, but only that it has been processed in a sterilizer. Such an indicator 44 may take the form of a chemical which reacts with a component in the sterilizing environment to form a new chemical with different properties, frequently a different color.

Among the important performance characteristics for chemical indicators are readability, reliability, selectivity, stability, and safety. "Readability" refers to the indicator characteristics which allow users to differentiate between unexposed indicators and those which have been exposed to sterilization conditions. "Good readability" means that virtually all health care workers, including those with common vision problems such as color blindness, can distinguish exposed indicators from unexposed indicators. For example, readability may be difficult when a user attempts to determine the shade of a color such as light brown turning to medium brown as the color change. Further, indicators should change in contrast as well as color. An indicator which changed, for example, from red to green, could pose problems for users with color vision defects unless there was an accompanying (sufficient) contrast change. Stability is also an important characteristic. The indicating means of both unexposed and exposed indicators must not change under ambient conditions.

Descriptions of various suitable chemical indicators may be found in the monograph "Biological and Chemical Indicators" Report 78-4.4 of the Health Industry Manufacturer's Association. Suitable chemical indicators may be selected from materials known to the art.

For purposes of illustration, it is worthwhile to consider a sterilization process such as that described in U.S. Pat. No. 5,084,239, in which items being sterilized are exposed to vapors of peracetic acid and acetic acid during one portion of the sterilization cycle. Embodiments of the invention preferably include a chemical indicator that changes color from a first color to a second color in response to acidic gas or vapor exposure. The first color is that which is observable when the indicator has not been exposed to acidic gas or vapor, but rather is the color at normal, ambient conditions (that is, the first color is the basic form of the pH sensitive dye). It is believed that particularly preferred indicators of this invention, as below further described and exemplified, actually respond to acetic acid vapor, which is a component of vaporized peracetic acid solution, and can also be formed by the breakdown of peracetic acid.

Dye compositions for inclusion on label 40 include a pH sensitive dye where the dye gives a color change, preferably at a pH approximately the same as or higher than the pK of the acidic fluid selected as the sterilant (or as a component in the sterilant gas or vapor) in the sterilization cycle being monitored. For example, although the pK of peracetic acid is about 9, the pK of acetic acid is about 4.75. Thus, the dyes for use with a peracetic acid exposure should change color at about 9 or at about 4.75 pH.

Among the preferred suitable pH sensitive dyes are 3',3",5',5"-tetrabromophenolsulfonephthalein (Bromophenol Blue), 3',3",5',5"-tetrabromo-m-cresol-sulfonephthalein (Bromocresol Green) and 5',5"-dibromo-o-cresolsulfonephthalein (Bromocresol Purple). Bromophenol Blue is blue at a pH of about 4.6, and turns yellow in the pH range between about 3 to 4.6. Bromocresol Green is blue at about pH 5.4, and turns yellow in the pH range between about 3.8 and 5.4. Bromocresol Purple turns from yellow to purple in the pH range between about 5.2 and 6.8. All these dyes have been determined to be stable so as to maintain their colors (initial and changed colors, respectively) under ambient conditions for at least about one year.

The dye compositions preferably include one or more conventional pH adjusting agents, binding agents, and/or thickening agents. The pH adjusting agents are useful to place the dye composition near or at the point where color change begins to occur. The binding and/or thickening agents may be selected from a wide range of binding and thickening agents known to the art, and are chosen so that they do not interfere with the dye activity.

With reference to FIG. 4, one sees the indicator 44 (here illustrated after exposure to an acidic fluid during a sterilization cycle and thus designated 44b), with a changed color that is lined to indicate the yellow color characteristic of the acidic form of Bromophenol Blue or Bromocresol Green. That is, the illustrated chemical indicator 44 is adapted to indicate visually whether exposure to an acidic fluid of a sterilization cycle has occurred by changing color from a first color (44a of FIG. 2) to a second color (44b of FIG. 4) such as in response to acidic gas or vapor exposure. One is not limited to a chemical indicator that only changes color in the presence of an acidic vapor, since other chemical indicator formulations would preferably be used in those situations in which the sterilizing agent is non-acidic.

Continuing with FIG. 4, label 40 is shown as having been affixed to second member 18 (such as by means of an adhesive) and the first and second members 16, 18 are together folded into an overlaying position along fold line 46 to form a flap 48 in which the tortuous path 36 is disposed. The flap 48 retards fluid communication beyond the fold line 46 by crimping the pathway at the position of the fold. The adhesive strip 42 assists in holding the flap in position. Perforations 50 (illustrated in FIG. 2) facilitate formation of the fold at the proper position. The flap is folded and secured into position prior to rupturing the glass ampule. However, a fastener can be used to hold the fold instead of or in addition to the adhesive strip.

As is illustrated also in FIG. 4, the ampule has been ruptured by pressing upon the deformable portion adjacent to cavity 20. One preferably holds the embodiment 10 in an upright, vertical position during or immediately after rupturing the ampule so the ampule contents can flow into contact with carrier 12. Indentations 52 as shown in FIGS. 1 and 2 are preferably formed in member 18 so as to lie on one side of ampule 14. Indentations 52 assist in seating the ampule 14 within cavity 20 and also give reaction points to help crush the ampule 14 when desired. Cavity 20 is also preferably configured with a dimpled area 54 as shown in FIGS. 1 and 2 to further assist in crushing the ampule 14 when desired.

An additional component that may accompany or be used with embodiment 10 can be a sleeve member (not illustrated) which may be placed around the exterior of ampule 14 to provide additional protection against any fragments from the ruptured ampule piercing the cavity 20 wall. Once ruptured, the ampule contents flow along passageway 38 and into contact with carrier 12. The spores are thus bathed in growth medium. If they are viable, they will germinate and begin to metabolize nutrients in the medium. One can visually observe the effects of such metabolism through use of a suitable growth detector as has already been described, and when cavity 22 is transparent.

With reference to FIGS. 5, 6 and 7 another embodiment of the invention is illustrated. This embodiment is particularly useful in monitoring a sterilizing apparatus or sterilizing process and comprises a plurality of indicator units.

Turning to FIG. 5, a single sheet 90 of a thermoformable material, such as has already been described, has had a plurality of tortuous paths 136, cavities 120 and cavities 122 formed in one portion 116 while the other portion 118 contains reaction points and is of a sufficient length to overlay portion 116 (as is seen in FIG. 6). A plurality of ampules 114 are dropped into respective cavities 120 and a plurality of carriers 112 dropped into the respective cavities 122.

Turning to FIG. 7, the portion 118 is then folded over portion 116 as an apparatus, or assemblage 100, which is then sealed, such as by RF sealing, while leaving a plurality of passageways 130 analogous to those previously described for embodiment 10.

The assemblage 100 can be shaped by diecutting with perforations 150 positioned appropriately so that one can readily fold into an overlaying position to form a flap 148 in which the plurality of tortuous paths 136 are disposed. However, since perforations 170 are also created generally parallel to each of the pathways 130, a user can separate one or more individual units of the assemblage 100 before use.

An advantage with both the embodiment 10 indicator illustrated by FIGS. 1–4 and the embodiment 100 indicator assemblage illustrated by FIGS. 5–7 is that after exposure to a sterilizing cycle, then the flaps 48, 148 can be selectively used to crimp or seal off the pathways 30, 130 so that foreign organisms cannot enter before the frangible ampule or ampules are broken and incubation has begun.

Aspects of the invention will now be illustrated with reference to several examples, which are intended to illustrate but not to limit the invention.

EXAMPLE 1

An assemblage of indicator embodiments was prepared with ten self-contained biological indicator units in each assemblage. The assemblage was formed from sheets of PETG with a thickness of 0.020 inch. The ampules included Bromocresol Purple as a chemical indicator and the carriers had spore populations ranging from $10^2$ to $10^8$ of *Bacillus circulans*. The tortuous paths each had an inner radius of $\frac{1}{32}$ (0.03) of an inch and had six bends of slightly greater than 90°. The ampules were about half-filled (0.6 milliliters) with the preferred growth medium as previously described.

EXAMPLE 2

Biological indicators prepared as described by Example 1, when the carriers each had spore populations of $10^6$ were used in monitoring a sterilizing apparatus and its process.

Thus, the biological indicators were exposed to sub-lethal and lethal sterilization cycles composed of peracetic acid vapor and plasma. Samples prepared with multiple populations of organisms and subjected to sub-lethal sterilization conditions resulted in fractional responses, that being a fraction of the units showed positive results (growth medium color change from purple to yellow). The units inoculated with lower populations showed no growth, while the units with higher populations showed growth. All samples exposed to full lethal sterilization conditions exhibited no growth.

It is to be understood that while the invention has been described above in conjunction with preferred specific embodiments, the description and examples are intended to illustrate and not limit the scope of the invention, which is defined by the scope of the appended claims.

It is claimed:

1. A biological indicator, comprising:

opposed first and second members, the first member including at least one deformable portion, the first and second members being held together and forming a pathway extending between an open end and a closed end, the pathway being configured as a tortuous path adjacent to the open end wherein the first and second members are constructed and positioned so as to be foldable into an overlaying position in which the tortuous path is disposed, the fold retarding fluid communication from the exterior at the open end of the pathway;

a selected microorganism being disposed along the pathway a spaced distance from the open end and downstream of the tortuous path; and a frangible ampule being sandwiched between the opposed members beneath the deformable portion, the ampule containing an aqueous medium, whereby sufficient externally applied pressure against the deformable portion will rupture the ampule, and the ampule and the selected microorganism will be placed in fluid communication when the ampule is ruptured.

2. The indicator as in claim 1 wherein the first member is formed of a flexible plastic film.

3. The indicator as in claim 2 wherein the second member is substantially planar, and the plastic film is adhered thereto.

4. The indicator as in claim 3 further including a tape affixed to the second member, the tape having a dye composition thereon that is substantially stable and capable of visually indicating whether exposure to a sterilization cycle has occurred.

5. The tape as in claim 4 wherein the dye composition changes color in response to exposure to a sterilizing medium.

6. The indicator as in claim 1 wherein the frangible ampule contains a fluid nutrient medium capable, with incubation, of promoting growth of the selected microorganism when contacted therewith.

7. The indicator as in claim 6 further comprising a detector material contained within the frangible ampule disposed along the pathway and placed in fluid communication with the selected microorganism when the ampule is ruptured, the detector material capable of undergoing a visible color change in response to growth of the selected microorganism.

8. The indicator as in claim 1 including an adhesive layer carried by at least one of the first and second members, the adhesive layer capable of adherently holding the overlaying position.

9. The biological indicator as in claim 1 wherein the opposed first and second members each define an indicator unit, and further comprising;

a plurality of indicator units formed with a common wall and being releasably attached to each other, each unit separable from an adjacent unit along a common edge, each unit including a carrier inoculated with a selected number of viable organism spores and a pathway in which the carrier is disposed, wherein each pathway is defined by the common wall and a second wall, each pathway being a spaced distance from the common edge and maintaining structural integrity when units are separated, the pathways being selectively placable into a substantially sealed off position.

10. The biological indicator as in claim 9 wherein at least one indicator unit includes organism spores different from those of another unit.

11. A process of making a biological indicator, comprising:

providing a cavity member sheet of deformable material having an initial surface with an axis there along and an edge intersecting the axis;

deforming the cavity member sheet to form a pathway protruding from the initial surface and generally extending in the direction of the axis from adjacent to the end, the pathway defining a first pathway portion adjacent to the edge, an interior pathway portion, and a middle pathway portion therebetween, the first pathway portion having at least one 90° angle with respect to the axis;

disposing a frangible ampule in the middle pathway portion and a carrier in the interior pathway portion, the frangible ampule having microorganism growth medium therein, the carrier having microorganism spores thereon;

sealing a backing member sheet to the initial surface; and, creating a fold line between the first pathway portion and the middle pathway portion, the fold line adapted to facilitate selectively crimping the pathway between the edge and the ampule and thereby retarding fluid communication into the pathway.

12. The process as in claim 11 wherein the first pathway portion has a serpentine configuration.

13. The process as in claim 11 wherein the cavity member sheet and the backing member sheet are portions of a single, thermoformable sheet, and the sealing step includes folding the backing member onto the initial surface of the cavity member.

14. The process as in claim 13 wherein the thermoformable sheet is a transparent or translucent polymer and the sealing step is by heat sealing.

* * * * *